(12) United States Patent
Zetina-Rocha et al.

(10) Patent No.: US 6,593,475 B1
(45) Date of Patent: Jul. 15, 2003

(54) PREPARATION OF DERIVATIVE OF 3-SULFONAMIDO-4-PHENYLAMINOPYRIDINE

(75) Inventors: Carlos B. Zetina-Rocha, Brantford (CA); Bhaskar Reddy Guntoori, Brantford (CA); Stephen E. Horne, Burlington (CA)

(73) Assignee: Brantford Chemicals Inc., Brantford (CA)

( * ) Notice: Subject to any disclaimer, the term of this patent is extended or adjusted under 35 U.S.C. 154(b) by 0 days.

(21) Appl. No.: 10/293,280

(22) Filed: Nov. 14, 2002

(30) Foreign Application Priority Data

Sep. 6, 2002 (CA) ............................................... 2401546

(51) Int. Cl.⁷ ............................................ C07D 213/71
(52) U.S. Cl. ...................................................... 546/293
(58) Field of Search ......................................... 546/293

(56) References Cited

U.S. PATENT DOCUMENTS 4,018,929 A * 4/1977 Delarge et al. ....... 260/294.8 F

* cited by examiner

*Primary Examiner*—Patricia L. Morris
(74) *Attorney, Agent, or Firm*—Marcelo K. Sarkis; Kitt Sinden; Ivor M. Hughes

(57) ABSTRACT

This invention relates to the preparation of 3-sulfonamido-4-arylaminopyridines by heating a 3-sulfonamido-4-aminopyridine with an aryl halide in the presence of an alkaline compound, a copper-containing agent and in the presence of a polar protic solvent.

19 Claims, No Drawings

PREPARATION OF DERIVATIVE OF 3-SULFONAMIDO-4-PHENYLAMINOPYRIDINE

FIELD OF INVENTION

The present invention relates to a new method for the preparation of disubstituted amines, and more particularly to a method for the preparation of a torsemide intermediate.

BACKGROUND OF THE INVENTION

Derivatives of 3-sulfonamido-4-phenylaminopyridine, of general formula I are key intermediates in the preparation of compounds with medicinally useful anti-inflammatory or diuretic properties. Some of the therapeutic properties of derivatives of this type are delineated in U.S. Pat. No. 4,018,929. An example of a medicament in this class is Torsemide (I, were $R_1$=3'-methyl; $R_2$=isopropylcarbamyl), which is marketed as an effective diuretic.

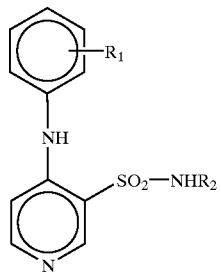

(I)

In the prior art, compounds such as I have traditionally been prepared by the reaction of a substituted aniline with a 3-substituted-4-halo-pyridine II with or without copper catalysis, as shown in Scheme 1 (U.S. Pat. Nos. 4,018,929 and 4,244,950). However, the synthesis of the required 3-substituted-4-halo-pyridine substrates (see J. Delarge, *Annales Pharmaceutiques Francaises* (1973), 31, 467–474) usually presents considerable preparative challenges such as drastic reaction conditions, elevated reaction temperatures (180–200° C.), use of toxic catalysts/reagents ($HgSO_4$, $PCl_5$, $POCl_3$) and formidable purification problems. In combination, these difficulties generally result in low yields of the product being obtained.

Scheme 1

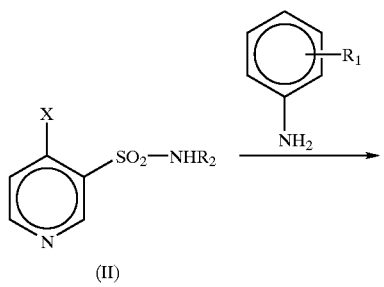

(II)

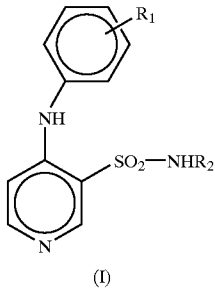

(I)

X = Halogen

This problem motivated us to find and alternative process for making derivatives of 3-sulfonamido-4-phenylaminopyridine I which gives high yields and uses substrates which can be more readily prepared, using milder reaction conditions and are easier to purify.

SUMMARY OF THE INVENTION

The deficiencies present in the processes described in the prior art would be overcome if compounds such as I were prepared instead by a different approach, such as using a 3-sulfonamido-4-aminopyridine III as the substrates for the coupling with an aryl halide (Scheme 2), given that the 3-sulfonamido-4-aminopyridine component III can be easily prepared from the readily available 4-aminopyridine and without the shortcomings encountered for the preparation of the substrates II. For examples of preparations of these substrates, see C. G. Neill, et al., *Tetrahedron* (1998), 54, 1365–16654, and E. J. Cragoe, Jr., et al., *Journal of Medicinal and Pharmaceutical Chemistry* (1961), 4, 369–383.

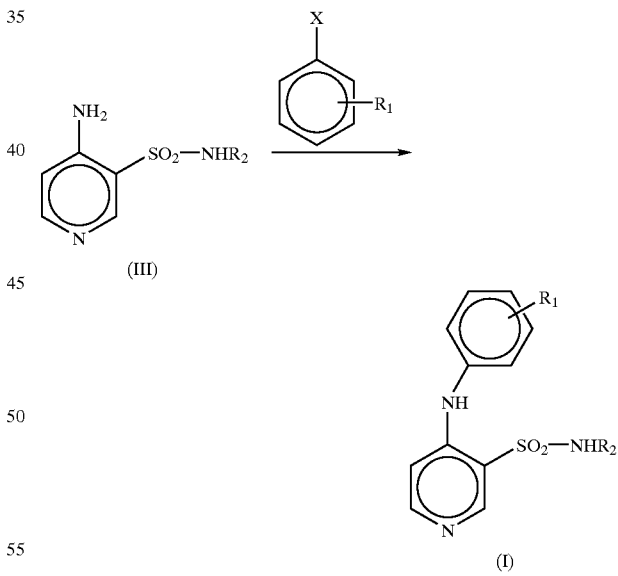

(III)

(I)

Unfortunately, the teachings of the prior art regarding a comparable reaction, between a substituted aniline with an aryl halide establishes that in the absence of strong electron-withdrawing groups in the aryl halide ring these compounds become less reactive (Inactivated) towards the desired condensation under the conditions previously described in the literature (for instance see, K. Nakamura et al. *Synthesis* (1974), 882–883; J. Lindley, *Tetrahedron* (1984), 40, 1433–1456; R. M. Acheson, *Acridines*, Interscience Division, John Wiley and Sons, New York (1956), p. 157).

Now, we have surprisingly found that 3-sulfonamido-4-arylaminopyridines such as I can be prepared by condensation of a 3-sulfonamido-4-aminopyridine III with an unactivated aryl halide such as IV when the reaction is carried out under a novel combination of reaction conditions, in the presence of an alkaline compound, a copper-containing agent, and in a protic polar solvent.

Thus, in accordance with an aspect of the present invention there is provided a process for preparing a compound of formula I:

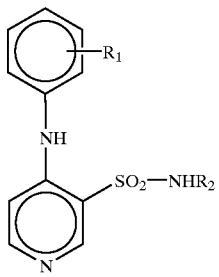

(I)

comprising the steps of: (i) heating a pyridine derivative of the formula III:

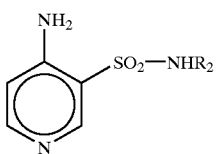

(III)

with an aryl halide of formula IV

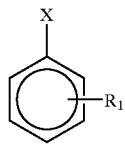

(IV)

in the presence of (iii) an alkaline compound;

(iv) a copper-containing agent; and (v) a protic polar solvent.

where $R_1$ represents hydrogen or a $C_1$–$C_4$-alkyl or alkenyl group, $R_2$ represents hydrogen or a group of the formula $R_3$OOC or a group of the formula $R_3$NHCO wherein $R_3$ represents a $C_1$–$C_4$-alkyl, alkenyl or unsubstituted or substituted phenyl group, and X represents Br or I.

This process is represented by the following equation:

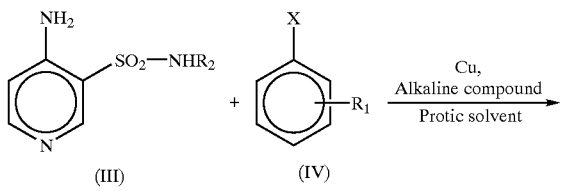

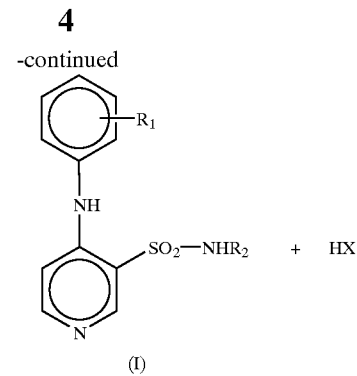

(I)

In a preferred embodiment of the present invention $R_2$ is hydrogen, $R_1$ is a 3'-methyl group and X is iodine, so that the aryl halide is 3-iodotoluene.

The alkaline compound includes, but is not limited to, potassium carbonate, potassium hydroxide, sodium carbonate, sodium hydroxide, lithium carbonate, lithium hydroxide, ammonium hydroxide and the like.

In another preferred embodiment of the present invention, the alkaline compound is potassium carbonate or potassium hydroxide. The preferred stoichiometric ratio of the alkaline compound is 1 to 5 moles per mole of compound III, more preferably 1.5 to 3.5 moles, most preferably 2.5 moles.

The copper-containing agent is one in which the copper is in a state of oxidation lower than 2. Thus, the copper may for example be in the form of the metal itself ($Cu^0$ with oxidation state of 0) or in the form of a Cu (I) salt ($Cu^1$ with an oxidation state of 1). Examples of these copper-containing agents include, but are not limited to, metallic copper, copper (I) oxide, copper (I) chloride, copper (I) bromide, copper (I) iodide, and copper (I) acetate. Metallic copper is the most preferred copper-containing agent for the reaction. The stoichiometry of the copper-containing agent is about 2 to 6 moles per mole of compound III, preferably 3 to 5 moles, most preferably 4 moles.

The process of the present invention is performed by heating the aryl halide and the 3-sulfonamido4-aminopyridine in the presence of a copper-containing agent in which the copper is in a state of oxidation lower than 2, and an alkaline compound in a suitable polar protic solvent.

When the reaction was carried out in the more usual solvents for this type of coupling, such as DMF, dioxane, toluene, etc., only trace amounts of the desired product I, or no product at all, was obtained. Furthermore, a number of unidentified byproducts were usually observed. Nevertheless, surprisingly we have discovered that by employing a novel combination of reaction conditions, these difficulties are resolved. In so doing, the number and amount of byproducts formed during the coupling reaction of an arninopyridine III and an aryl halide IV are substantially reduced, thereby increasing the yield of I.

Examples of polar protic solvents which are useful in the reaction of the present invention include, but are not limited to, n-propanol, isopropanol, n-butanol, amyl alcohol and ethylene glycol. n-Butanol is the most preferred solvent for this process.

The process of the present invention also uses a minimum temperature of about 80° C. The reaction is conducted at a temperature between the range of about 80° C. and about 180° C. Most preferably the reaction temperature is maintained within the range of about 115° C. to about 130° C. The reaction is preferably carried out under an inert atmosphere, for example under argon or nitrogen.

Thus, according to a preferred embodiment of the invention, the reaction is conducted by heating at about 120°

C. a mixture of about 1.5 moles of the selected aryl halide with about one mole of the 3-sulfonamido-4-aminopyridine and about 2.5 moles of potassium carbonate in the presence of about 4 moles of copper metal and n-butanol as a solvent.

The following examples illustrates the preparation of compounds of formula I and are not to be construed as limiting the scope of the invention in any manner.

EXAMPLE 1

Preparation of 3-Sulfonamido-4-(3'-methylphenyl) aminopyridine (formula I: $R_1$=3'-Methyl; $R_2$=H). Method A.

To an oven dried flask equipped with magnetic stirrer, condenser and thermometer and cooled under nitrogen was added 3-sulfonamido-4-amino pyridine (2.0 g, 11.5 mmol), 3-iodotoluene (3.77 g, 17.2 mmol), potassium carbonate (4.0 g, 28.9 mmol), and n-butanol (20 mL) and the suspension was stirred for 10 minutes, at which point copper (2.94 g, 46.2 mmol) was added. The mixture was heated to 118° C. and stirring was continued for about 24 h. The reaction mixture was cooled to 45–50° C. and a mixture of methanol-water (70:30 v/v) was added. The reaction mixture was filtered through a pad of Celite™. The solution was evaporated under vacuum to 9 mL, then water (10 mL) was added and the mixture was evaporated to 9 mL. Another portion of water (10 mL) was added and the mixture was evaporated again to 9 mL. Water (12 mL) and a saturated sodium thiosulfate solution (5 mL) was added and the mixture was stirred for 45 minutes. The mixture was extracted twice with dichloromethane (24 mL total) and the organic phase was evaporated to dryness under vacuum. Water (12 mL) was added and the solution was acidified to pH=6 with glacial acetic acid (1 mL). The mixture was evaporated to dryness under vacuum. Ethanol (15 mL) was added and the mixture evaporated to dryness under vacuum. The crude mixture was chromatographed on silica gel (initially 4% methanol in dichloromethane, then polarity increased to 9% methanol in dichloromethane), to give 3-sulfonamido-4-(3'-methylphenyl) aminopyridine as a white powder (1.61 g, 53.1% yield). Mass spectral data: Direct electron impact: 264 (M+1, 100%). $^1$H NMR (DMSO-$d_6$) δ: 8.65 (s, 1H), 8.24 (d, 1H, J=5.5 Hz), 8.05 (s, 1H, $D_2O$ exchangeable), 7.76 (s, 2H, $D_2O$ exchangeable), 7.33 (dd, 1H, J=7.54, 7.51 Hz), 7.12–7.04 (m, 3H), 6.98 (d, 1H, J=5.5 Hz), 2.33 (s, 3H). $^{13}$C NMR (DMSO-$d_6$) δ: 152.69, 149.04, 147.30, 139.20, 138.58, 138.08, 129.42, 126.03, 124.11, 122.98, 120.59, 107.83, 20.89. A small amount of a dialkylated compound I, where $R_1$ was 3'-methyl and $R_2$ was 3"-methylphenyl was also isolated.

EXAMPLE 2

Preparation of 3-Sulfonamido4-(3'-methylphenyl) aminopyridine (formula I: $R_1$=3'-Methyl; $R_2$=H). Method B.

An oven dried round-bottomed flask equipped with magnetic stirrer, condenser and thermometer was cooled under nitrogen and was charged with 3-sulfonamido-4-amino-pyridine (1.0 g, 5.8 mmol), 3-iodotoluene (1.76 g, 8.1 mmol), copper (I) oxide (3.71 g, 25.9 mmol), potassium carbonate (2.39 g, 17.3 mmol) and n-propanol (16 mL). The mixture was heated to reflux (97° C.) and stirring was continued for about 36 h. The reaction mixture was then worked-up in similar manner as indicated in method A above. The crude product was purified by chromatography on silica gel, eluting with mixture dichloromethane-methanol 96:4 to give 0.68 g, 44.7% yield of the above titled compound.

While the foregoing provides a detailed description of the preferred embodiment of the invention, it is to be understood that the description is illustrative only of the principles of the invention and not limiting. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for preparing a compound of formula I:

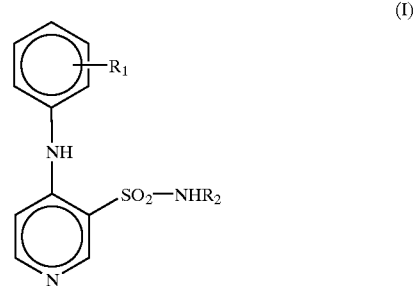

comprising the steps of:
(i) heating a pyridine derivative of formula III:

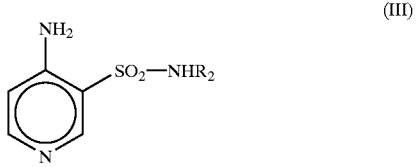

with an aryl halide of formula IV

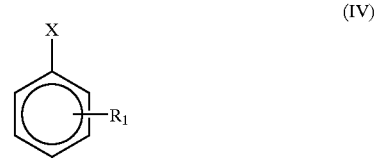

where $R_1$ represents hydrogen or a $C_1$–$C_4$-alkyl or alkenyl group, $R_2$ represents hydrogen or a group of the formula $R_3$OOC or a group of the formula $R_3$NHCO wherein $R_3$ represents a $C_1$–$C_4$-alkyl, alkenyl or unsubstituted or substituted phenyl group, and X represents Br or I;
in the presence of
(iii) an alkaline compound;
(iv) a copper-containing agent and
(v) a protic polar solvent.

2. The process of claim 1, wherein the alkaline compound is selected from potassium carbonate, potassium hydroxide, sodium carbonate, sodium hydroxide, lithium carbonate, lithium hydroxide, and ammonium hydroxide.

3. The process of claim 1, where the alkaline compound is potassium carbonate.

4. The process of claim 1, wherein the copper-containing agent is selected from metallic copper, copper (I) oxide, copper (I) chloride, copper (I) bromide, copper (I) iodide, and copper (I) acetate.

5. The process of claim 1, wherein the copper-containing agent is metallic copper.

6. The process of claim 1, wherein the polar protic solvent is selected from ethylene glycol, amyl alcohol, n-butanol, n-propanol and isopropanol.

7. The process of claim 1, where the polar protic solvent is n-butanol.

8. The process of claim 1, wherein $R_2$ is hydrogen.

9. The process of claim 1, wherein the heating is carried out at a temperature of about 80° C. to about 180° C.

10. The process of claim 1, wherein the heating is carried out at a temperature of about 115° C. to about 130° C.

11. The process of claim 1, 2, 3, 4, 5, 6, 7, 8, 9 or 10 wherein the aryl halide is 3-iodotoluene.

12. The process of claim 1, 2, 3, 4, 6, 7, 8, 9 or 10, wherein the copper-containing agent is in a stoichiometric ratio of 2 to 6 with respect to the compound of formula III.

13. The process of claim 1, 2, 3, 4, 6, 7, 8, 9 or 10, wherein copper-containing agent is in a stoichiometric ratio of 4 with respect to the compound of formula III.

14. The process of claim 1, 2, 3, 4, 6, 7, 8, 9 or 10, wherein the alkaline compound is in a stoichiometric ratio of 1 to 5 with respect to the compound of formula III.

15. The process of claim 1, 2, 3, 4, 6, 7, 8, 9 or 10, wherein the alkaline compound is in a stoichiometric ratio of 2.5 with respect to the compound of formula III.

16. The process of claim 11, wherein the copper-containing agent is in a stoichiometric ratio of 2 to 6 with respect to the compound of formula III.

17. The process of claim 11, wherein copper-containing agent is in a stoichiometric ratio of 4 with respect to the compound of formula III.

18. The process of claim 11, wherein the alkaline compound is in a stoichiometric ratio of 1 to 5 with respect to the compound of formula III.

19. The process of claim 11, wherein the alkaline compound is in a stoichiometric ratio of 2.5 with respect to the compound of formula III.

* * * * *